United States Patent
Hwu et al.

(10) Patent No.: US 9,150,688 B2
(45) Date of Patent: Oct. 6, 2015

(54) COPOLYMER, COMPLEX AND METHOD FOR RELEASING VIRUSES USING PH-DEPENDENCE OF THE COPOLYMER

(75) Inventors: Yeu Kuang Hwu, Taipei (TW); S Ja Tseng, Taipei (TW)

(73) Assignee: INSTITUTE OF PHYSICS, ACADEMIA SINICA, Taipei (TW)

( * ) Notice: Subject to any disclaimer, the term of this patent is extended or adjusted under 35 U.S.C. 154(b) by 691 days.

(21) Appl. No.: 13/459,894

(22) Filed: Apr. 30, 2012

(65) Prior Publication Data
US 2013/0288337 A1    Oct. 31, 2013

(51) Int. Cl.
*C08G 63/685*    (2006.01)
*C08L 67/04*     (2006.01)
*C12N 7/00*      (2006.01)

(52) U.S. Cl.
CPC ............... *C08G 63/685* (2013.01); *C08L 67/04* (2013.01); *C12N 7/00* (2013.01)

(58) Field of Classification Search
CPC ...... C08G 63/685; C08G 73/02; C08L 67/04; C12N 7/00
USPC ....... 528/289; 525/421; 435/235.1; 424/93.6, 424/196.11, 486, 193.1
See application file for complete search history.

(56) References Cited

U.S. PATENT DOCUMENTS 8,697,858 B2    4/2014    Iversen

FOREIGN PATENT DOCUMENTS

TW    201121550 A1    7/2011
TW    102113241       1/2015

OTHER PUBLICATIONS

Anderson et al. (Advanced Materials, Published 2006, pp. 2614-2618).*
Lynn et al. (J. Am. Chem. Soc., Published 2001, pp. 8155-8156).*
Piyush Chaturbedy et al., "pH-Sensitive Breathing of Clay within the Polyelectrolyte Matrix," www.acsnano.org, vol. 4, No. 10, pp. 5921-5929, 2010.
Guang Hui Gao et al., "pH-responsive polymeric micelle based on PEG-poly(β-amino ester)/(amido amine) as intelligent vehicle for magnetic resonance imaging in detection of cerebral ischemic area," Journal of Controlled Release 155 (2011) 11-17.
Samuel H. Crayton et al., "pH-Titratable Superparamagnetic Iron Oxide for Improved Nanoparticle Accumulation in Acidic Tumor Microenvironments," www.acsnano.org, vol. 5, No. 12, pp. 9592-9601, 2011.
Sang-Min Lee et al., "Triggered Release of Pharmacophores from [Ni(HAsO3)]-Loaded Polymer-Caged Nanobin Enhances Pro-apoptotic Activity: A Combined Experimental and Theoretical Study," www.acsnano.org, vol. 5, No. 5, pp. 3961-3969, 2011.
Xian-Zhu Yang et al., "Sheddable Ternary Nanoparticles for Tumor Acidity-Targeted siRNA Delivery," www.acsnano.org, Published online 10.1021/nn204240b, pp. A-K, 2011.
Chung-Huei K. Wang et al., "The transduction of Coxsackie and Adenovirus Receptor-negative cells and protection against neutralizing antibodies by HPMA-co-oligolysine copolymer-coated adenovirus," Biomaterials 32 (2011) 9536-9545.

* cited by examiner

*Primary Examiner* — Richard Schnizer
*Assistant Examiner* — Alma Pipic
(74) *Attorney, Agent, or Firm* — Ming Chow; Sinorica, LLC (57) ABSTRACT

A method for releasing viruses includes the steps of: preparing a first negatively charged complex, comprising a plurality of viruses, a plurality of polyethyleneimine particles, and a copolymer; transferring the complex to an acidic region, thereby transforming the complex into a positively charged complex to release a portion of the viruses in the acidic region; and transferring the complex to a non-acidic region, thereby transforming the positively charged complex into a negatively charged complex. One embodiment of the copolymer has the following chemical formula:

wherein R1 represents aliphatic compounds or aromatic compounds, and R2 includes at least one negatively charged group.

**18 Claims, 11

FIG. 1

1-(3-aminopropyl)imidazole (ApIm)

DL-Aspartic acid (Asp)

Copolymerization
DMSO
65 – 75°C, 120 hr

Poly(ethylene glycol) (PEG) diacrylate poly(PEG-ApIm-PEG-Asp)

COPOLYMER, COMPLEX AND METHOD FOR RELEASING VIRUSES USING PH-DEPENDENCE OF THE COPOLYMER

TECHNICAL FIELD

The present disclosure relates to a copolymer, complex and method for releasing viruses using pH-dependence of the copolymer, and more particularly, to a copolymer, complex and method for releasing viruses using charge reversal and size oscillation through the pH-dependence of the copolymer.

BACKGROUND ART

The carrier or vehicle with pH-sensitive property has been cited frequently as a promising vector for controlled drug delivery when the system is turned to respond to change in a window of physiologically relevant condition. The pH-responsive vectors utilizing the acidic intracellular environment via proton buffer effect or reversible PEG shielding were extensively synthesized in the past. However, successful development of such a technology involves individual components that are not only capable of sensing minute physiologically changes in environment but that can also respond to such changes in the vectors. Therefore, the pH-responsive vehicle is a valuable component of stimuli-responsive mechanisms to trigger the wherein R1 represents aliphatic compounds or aromatic compounds, and R2 includes at least one negatively charged group.

Another embodiment of the present disclosure provides a method for releasing viruses comprising the steps of: preparing a first negatively charged complex, comprising a plurality of viruses, a plurality of polyethyleneimine particles, and a copolymer having the following chemical formula:

wherein R1 represents aliphatic compounds or aromatic compounds, and R2 includes at least one negatively charged group; transferring the complex to an acidic region, thereby transforming the complex into a positively charged complex to release a portion of the viruses in the acidic region; and transferring the complex to a non-acidic region, thereby transforming the positively charged complex into a negatively charged complex.

The foregoing has outlined rather broadly the features and technical advantages of the present disclosure in order that the detailed description of the disclosure that follows may be better understood. Additional features and advantages of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

The objectives and advantages of the present disclosure are illustrated with the following description and upon reference to the accompanying drawings in which.

DETAILED DESCRIPTION

Figure 1:
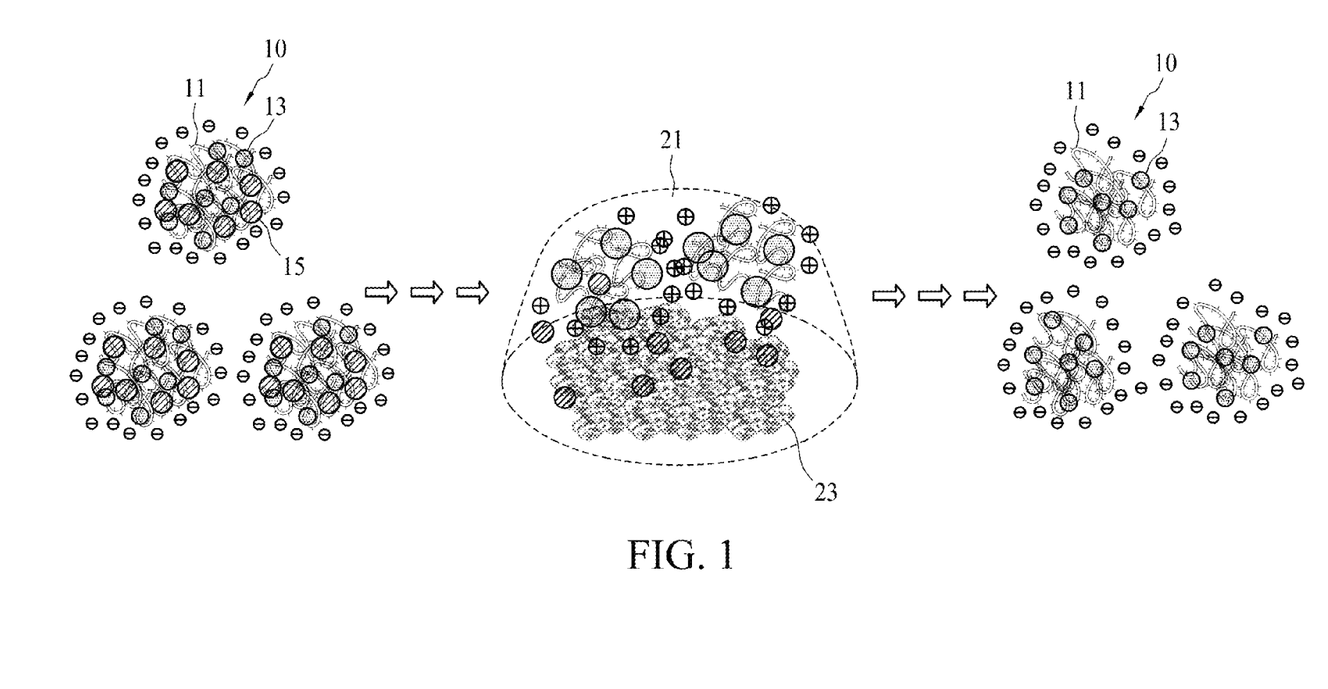
FIG. 1 is a schematic diagram illustrating complex-mediated extracellular release of viruses by pH-dependent charge reversal and size oscillation for localized delivery according to one embodiment of the present disclosure. The viruses of the complex are released in response to extracellular (tumor) acid conditions, and the complex becomes a reversible structure after the virus is released from the complex.

In one embodiment of the present disclosure, our approach was schematically presented in FIG. 1. In one embodiment of the present disclosure, we prepared a negatively charged complex 10 comprising a plurality of viruses 15 such as adeno-associated virus serotype 2 (AAV2), a plurality of positively charged polymers 13, and a copolymer 11 having the following chemical formula:

wherein R1 represents aliphatic compounds or aromatic compounds, and R2 includes at least one negatively charged group.

In one embodiment of the present disclosure, n is between 20 and 30 and m is between 2 and 10, the copolymer 11 has a weight-average molecular weight from 19,000 to 21,600 and a polydispersity index from 1.5 to 1.9. In one embodiment of the present disclosure, the copolymer 11 is negatively charged above pH 7.4 and positively charged below pH 6.5.

In this disclosure, we provide a new method and demonstrate its capability to accurately release viruses locally. In one embodiment of the present disclosure, we synthesized the biodegradable and pH-sensitive copolymer 11 containing specific pKa (logarithmic acid-ionization constant) of the 1-(3-aminopropyl)imidazole (ApIm) and DL-aspartic acid (Asp) for pH-sensitive adjustment. The amine group of imidazole ring or the carboxylic acid group of Asp is allowed to form a positive charge or a negative charge in physiological pH ranges. The hydrophilic segment of poly(ethylene glycol) (PEG) as a linker of ApIm and Asp is non-immunogenic and resistance of non-specific protein adsorption. In one embodiment of the present disclosure, we selected the recombinant AAV2, which has shown promising results as the delivery virus in human clinical trials with fewer safety concerns.

As the negatively charged complex 10 is transferred to an acidic region 21 such as the extracellular (tumor 23) acid condition, the exposure of the complex 10 to acidic pH triggered the in situ charge reversal (positively charged) and size oscillation, and this was followed by the release of AAV2 15 from the complex 10. The complex 10 recovered and reformed the original shape once the environment returned from the acid region 21 to a neutral region. Here, we have shown the charge reversal, size oscillation, reversible change to the size of the complex via a pH-responsive trigger that allowed the release of AAV2. We also evaluated the activity of AAV2 released from the complex at different pH values, and the AAV2-mediated transformation efficiency was calculated by Flow cytometry analysis.

Materials

In one embodiment of the present disclosure, poly(ethylene glycol) (PEG) diacrylate (Mn=258, density=1.11 g mL$^{-1}$), 1-(3-aminopropyl)imidazole (ApIm, density=1.049 g mL$^{-1}$), DL-aspartic acid (Asp) magnesium salt, and polyethyleneimine (PEI$_{800}$, Mw=800) were purchased from Aldrich (Milwaukee, Mich.). Diethyl ether and phosphate buffered saline (PBS) were purchased from Sigma Co. (St. Louis, Mo.). Dimethyl sulfoxide (DMSO) was purchased from Hula (Buchs, Switzerland). CellTiter 96 AQueous One solution for the MTS assay was purchased from Promega (Madison, Wis.). Recombinant AAV2-GFP control virus (adeno-associated virus serotype 2; green fluorescent protein; concentration=1×10$^{12}$ GC/mL) was purchased from Cell Biolabs (San Diego, Calif.). For preparation of fluorescent labled-AAV2, AAV2 stocks were labeled with Alexa Fluor 488 fluorescent dye using a protein-labeling kit from Molecular Probes (Eugene, Oreg.). Labeled virus was further purified according to the protocol.

Synthesis and Purification of poly(PEG-ApIm-PEG-Asp) copolymer

Figure 2:
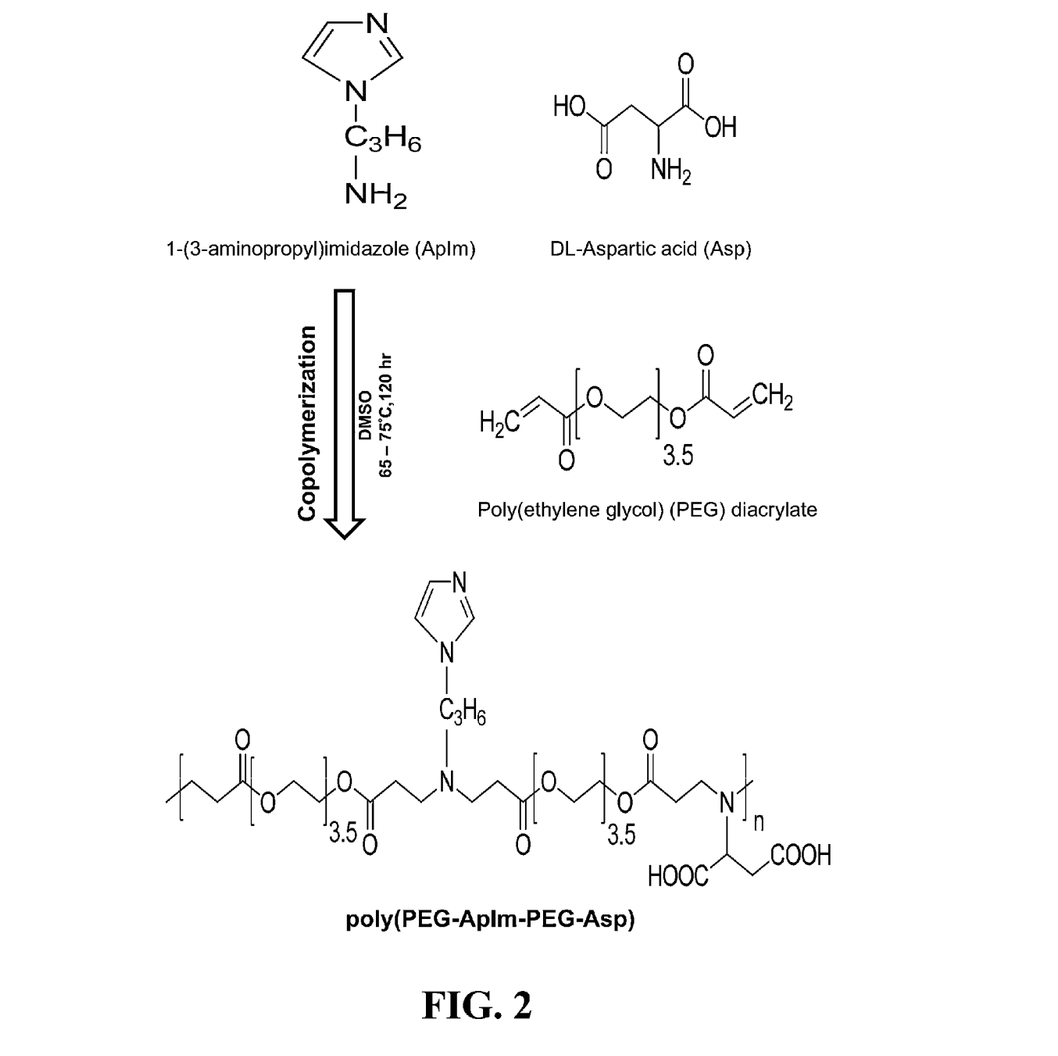
FIG. 2 shows the synthesis of the poly(PEG-ApIm-PEG-Asp) copolymer according to one embodiment of the present disclosure.

Referring to FIG. 2, the copolymerization of ApIm, Asp, and PEG diacrylate was performed in DMSO solution using a parallel synthesizer connected to a vacuum line with the vacuum (±0.2 mmHg) controlled by a digital vacuum controller. Copolymer, poly(PEG-ApIm-PEG-Asp), was prepared according to previously reported procedures as shown in FIG. 2. In a typical experiment, reaction mixtures were prepared, and contained ApIm (27.4 mg, 0.219 mmol), Asp magnesium salt (79.0 mg, 0.219 mmol), and DMSO solvent, and the reaction mixtures were then stirred at room temperature for 1 hour to achieve a homogeneous solution. A PEG diacrylate (101.5 μL, 0.437 mmole) was added dropwise to the mixture solution, and then heated in a constant temperature oil bath at 65-75° C. for 120 hours. The copolymers products were isolated and purified according to the following procedures. The obtained yellow colloid of copolymers were subsequently washed with diethyl ether (10.0 mL) three times and dried at 40° C. under high vacuum (1.0 mmHg) for 16 hours. We also synthesized the poly(PEG-ApIm) and poly (PEG-Asp) via common copolymerization as described above.

Characterization of Synthesized Copolymer

The synthesized copolymer was examined by nuclear magnetic resonance (NMR, Varian Unity Inova 500 MHz spectrometer). Chemical shifts of $^1$H NMR spectra are reported in parts per million against residual solvent resonance as the internal standard. 99.8% pure DMSO-d6 was used as the solvent in characterization. The molecular weights of the copolymers were determined by high-performance liquid chromatography/gel permeation chromatography analysis (HPLC/GPC, Waters model LC-2410). THF was used as the eluent, and polystyrene was used as the reference in HPLC/GPC. The flow rate was 1.0 mL min$^{-1}$. The weight- and number-average molecular weights (Mw and Mn, respectively) were calibrated with using polystyrene standards.

Acid-base titration was used to evaluate the pH-sensitive region of synthesized copolymers. Approximately 10.0 mg of the copolymers was dissolved in 10.0 mL of PBS solution, and 1.5 mL of 1 N NaOH solution was then added to the solution to adjust the pH to the alkaline range of approximately 11.5. Approximately 0.1 N HCl was used as the titratant to lower the pH to acidic conditions of approximately 2.5.

Cell Culture and Cell Viability Analysis by MTS Assay

Human cervical carcinoma HeLa cells (CCL-2, ATCC) was maintained in DMEM (Dulbecco's modified Eagle's minimum essential medium, Invitrogen), supplemented with 10% fetal bovine serum (FBS), 100 U mL$^{-1}$ penicillin, and 100 μg mL$^{-1}$ streptomycin at 37° C. in a humidified atmosphere of 5% $CO_2$.

$10^5$ HeLa cells were seeded in each of the wells of a 24-well plate and fed with complete medium for 12 hours. The cells were then exposed to the copolymers at a particular concentration (0.1, 0.2, 0.5, 1.0, and 1.5 mg mL$^{-1}$) and incubated for 24 hours. The CellTiter 96® AQueous One solution cell proliferation assay system with the tetrazolium compound (3-(4,5-dimethylthiazol-2-yl)-5-(3-carboxymethoxyphenyl)-2-(4-sulfophen yl)-2H-tetrazolium, inner salt; MTS) was used to measure the survival rate and proliferation of mammalian cells. The optical density (OD) of formazan at 490 nm quantified the cell viability. The reduction of MTS achieved by untreated cells was set at 100%, and that of the cells was expressed as a percentage of untreated cells. Data are shown as the mean±the standard error for three independent experiments performed in triplicate.

Preparation and Characterization of Complex

AAV2-based copolymeric complex at various known weight ratios (w/w) of poly(PEG-ApIm-PEG-Asp)/$PEI_{800}$ (1/1, 2/1, 3/1, 5/1, and 10/1) were prepared by an electrostatic method in deionized (DI) water (pH 7.4). Briefly, an aqueous AAV2 solution (1 μL, 1×$10^9$ GC μL$^{-1}$) was mixed with an aqueous poly(PEG-ApIm-PEG-Asp) solution at a 2.0 μg with a final volume of 100 μL for forming complex. The complex were obtained upon addition of the complex solution, using a pipette, into an aqueous $PEI_{800}$ (0.1 μg μL$^{-1}$) and then thoroughly mixed for 30-60 seconds by vortex and left for at least 0.5 hour at room temperature before measurements.

The hydrodynamic diameter and the zeta potential measurements at different pH were carried out using Zetasizer Nano ZS (Malvern Instruments). The temperature for the measurement was kept at 25° C. The concentration of the samples was 0.03% w/v. The pH of the solutions was adjusted using 0.5 M aqueous HCl/NaOH solutions.

TEM images were then acquired on a JEOL-1010 microscope operating at an accelerating voltage of 100 kV. A drop of the complex solution was allowed to air-dry on a Formvar-carbon-coated 200 mesh copper grid.

pH-Dependence Complex-Mediated AAV2 Transformation

Approximately $10^5$ HeLa cells were added to each of the wells of a 24-well plate for 12 hours prior to transformation. Subsequently, a porous polyester Transwell™ insert (Corning, N.Y.) with a pore size of 0.4 μm was placed above the cell monolayer (in one well of a 24-well dish) to separate the AAV2-poly(PEG-ApIm-PEG-Asp)/$PEI_{800}$ complex (Transwell™ insert) and the target HeLa cells (24-well dish). Then the AAV2-poly(PEG-ApIm-PEG-Asp)/$PEI_{800}$ complex were prepared in only DMEM (0.5 mL) at different pH values (pH 4.0, 5.5, 6.0, 6.5, 7.0 or 7.4), and the transformation cocktail were then incubated for 6 hours with gentle incubation to release the AAV2 from the AAV2-poly(PEG-ApIm-PEG-Asp)/$PEI_{800}$ complex. Six hours later, the Transwell™ insert was removed. Cells were incubated for an additional 7 days before reporter analysis. The complete DMEM medium was replaced daily. The only AAV2-treated cells are the positive control. In vitro infection, infectious AAV2 amount (5,000-10,000 GC/cells) was performed according to the protocol of the AAV2-GFP Control Virus System using cells as targets for transformation.

Analysis of Reporter Expression

The AAV2 were incorporated in the complex, and their release was evaluated by measuring GFP intensities. Flow cytometry analysis of GFP-transfected cells was conducted with a benchtop system (FACSCalibur, Becton Dickinson) equipped with a 488 nm argon laser and a band-pass filter at 505-530 nm to detect GFP. Untransfected cells were used as the control. The cells were appropriately gated by forward and side scatters, and 10,000 events per sample were collected. The GFP-transfected cells were then directly observed by a confocal microscope (Olympus IX 70, Olympus). The cells transfected with AAV2 were stained overnight by propidium iodide (PI, Molecular Probes, Eugene, Oreg., USA) to label the nuclei.

Characterization of poly(PEG-ApIm-PEG-Asp)

The designed poly(PEG-ApIm-PEG-Asp) copolymer were successfully copolymerized form the poly(ethane glycol) (PEG) diacrylate, 1-(3-aminopropyl)imidazole (ApIm), and DL-aspartic acid (Asp). The designated functional groups and copolymer structure were confirmed by the $^1$H NMR spectra. The typical $^1$H NMR signals, δ (ppm) 11.5 (H of carboxylic acid), 6.9, 7.2, 7.8 (H of imidazole compound), 3.6 (H of PEG compound), 2.4, 2.4-2.7 (—O—C(O)—$CH_2$—$CH_2$—$N(CH_2)$—, —$N(CH_2)$—$CH_2$—$CH_2$—$CH_2$—N(CH)—, —CH(N)—$CH_2$—C(O)—OH), 3.7-3.9 (—O—C(O)—$CH_2$—$CH_2$—$N(CH_2)$—, —$N(CH_2)$—$CH_2$—$CH_2$—$CH_2$—N(CH)—, —CH(N)—$CH_2$—C(O)—OH) were used to confirm the chemical structure of poly(PEG-ApIm-PEG-Asp) copolymer. The weight-average molecular weight (Mw) of poly(PEG-ApIm-PEG-Asp) was determined by high-performance liquid chromatography/gel permeation chromatography analysis (HPLC/GPC). The poly(PEG-ApIm-PEG-Asp) has a Mw of 19,000-21,600 and a polydispersity index (PDI) of 1.5-1.9.

Figure 3:
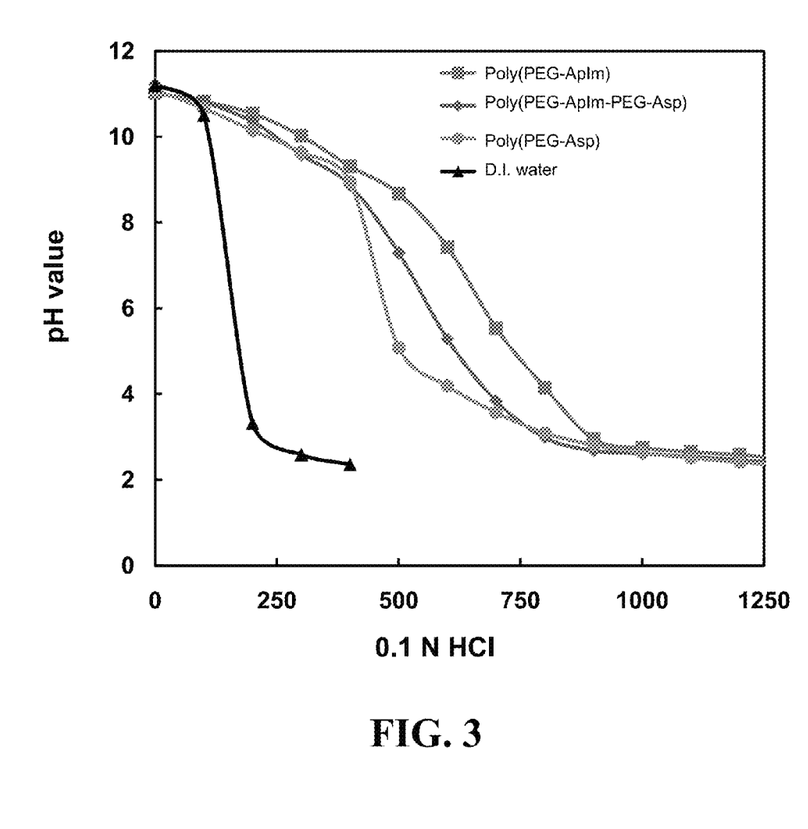
FIG. 3 shows acid-base titration of native copolymers according to one embodiment of the present disclosure. The solution was prepared in PBS solution at a copolymer of 10 mg mL$^{-1}$.

Due to the unique pKa (logarithmic acid-ionization constant) of specific structure, these structures are commonly used in pH-sensitive delivery of drug and nucleic acid. The titration curve for the tested poly(PEG-ApIm-PEG-Asp) is used to empirically estimate its pH-sensitive regions. With the ApIm in copolymer (poly(PEG-ApIm)), the extent of pH-sensitive region was significantly enhanced from a large portion of Asp consisting of copolymer (poly(PEG-Asp)) (FIG. 3) to pH 3.47-9.40. It is well known that the ionizable amine group of imidazole side-chain existed in an acidic environment mainly forms the positively charged of its side chain structure. Consequently, the pH-sensitive adjustment of synthesized poly(PEG-ApIm-PEG-Asp) might be due to the major factor: the amine component of imidazoly group in copoylmer. It was likely that a large fraction of ApIm were mixed with Asp and further copolymerized with PEG diacrylate during the synthesis of poly(PEG-ApIm-PEG-Asp), resulting in an extremely buffer capacity.

Cytotoxicities of poly(PEG-ApIm-PEG-Asp)

Figure 4:
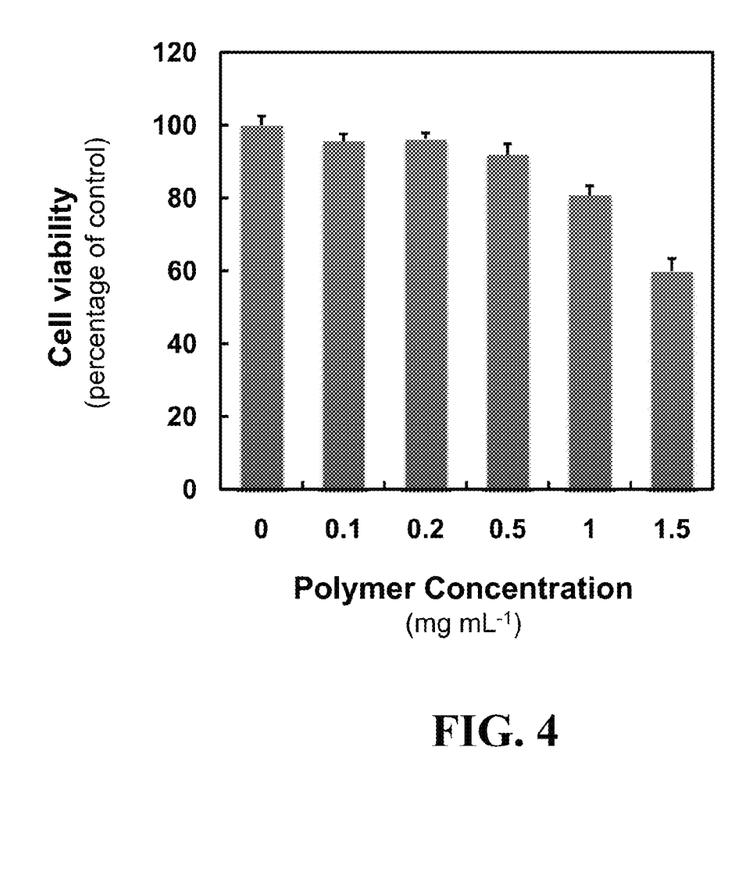
FIG. 4 shows viability of HeLa cells after treatment with free polymer or polymer at concentration variation (mg mL$^{-1}$) according to one embodiment of the present disclosure. Cell viability is given as the percentage of viable cells remaining after treatment for 24 hours, compared to the control free copolymer-treated cells. Cell number was determined by the standard MTS assay. Results were carried out in triplicate and the standard deviation is shown by the error bars.

To qualify as a carrier, the foremost requirement is the free of cytotoxicity. A 0.500 mg mL$^{-1}$ of synthesized poly(PEG-ApIm-PEG-Asp) reduced cell viability by less than 10% upon incubation mimicking an irretrievable condition of in vivo administration (FIG. 4). When the tested copolymer concentration was increased to 1.0 mg mL$^{-1}$, the viabilities of the cells that were treated with the copolymers were ~80%. Even when the concentration of the poly(PEG-ApIm-PEG-Asp) was as high as 1.5 mg mL$^{-1}$, the cell viability was >60%, indicating that the poly(PEG-ApIm-PEG-Asp) exhibited low toxicity toward the target cells. However, poly(PEG-ApIm-PEG-Asp) will be degraded by hydrolysis of its ester linkages in the presence of water. Note that the poly(PEG-ApIm-PEG-Asp) consisting of PEG segment, amino acid, and biodegradable ester linker becomes more biocompatible.

As well being able to deliver AAV2 and be effective in nanomedicine, a successful major composite of complex should exhibit minimal cytotoxicity. A 0.500 mg mL$^{-1}$ of synthesized poly(PEG-ApIm-PEG-Asp) reduced cell viability by less than 10% upon incubation mimicking an irretrievable condition of in vivo administration (FIG. 4). When the copolymer concentration was increased to 1.0 mg mL$^{-1}$, the viabilities of the cells that were treated with the copolymers were approximately 80%. Significantly, even when the concentration of the poly(PEG-ApIm-PEG-Asp) was as high as 1.5 mg mL$^{-1}$, the cell viability was still 60%, indicating that the poly(PEG-ApIm-PEG-Asp) exhibited low toxicity toward the target cells. However, poly(PEG-ApIm-PEG-Asp) will be degraded by hydrolysis of its ester linkages in the presence of water. Therefore, it is important to note that the poly(PEG-ApIm-PEG-Asp) consisting of PEG segment, amino acid, and biodegradable ester linker becomes more and more biocompatible as the copolymer concentration is increased.

Figure 5:
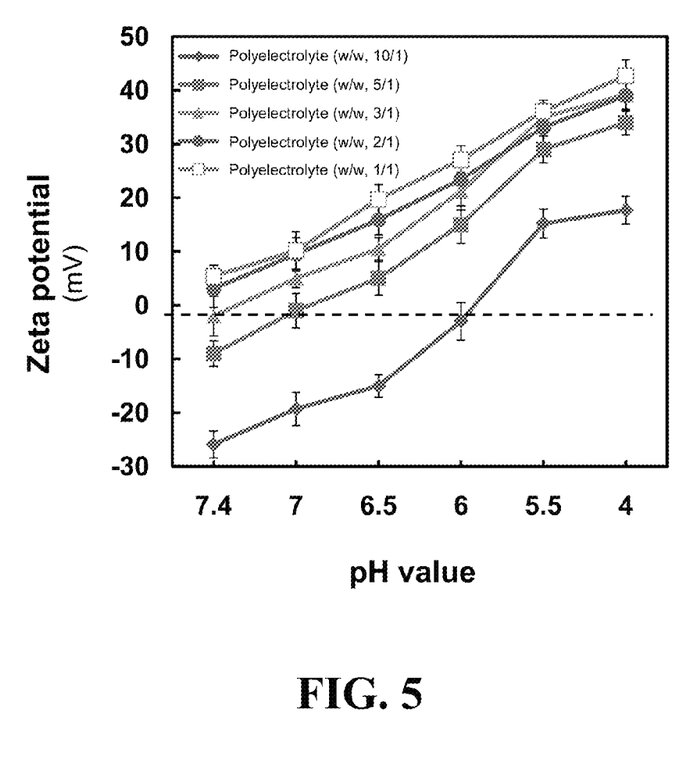
FIG. 5 is a plot of zeta potential of AAV2-poly(PEG-ApIm-PEG-Asp)/PEI$_{800}$ complex vs. pH variation according to one embodiment of the present disclosure. For preparation of the complex at different weight ratios (w/w), the adeno-associated virus serotype 2 (AAV2) was first mixed with poly(PEG-ApIm-PEG-Asp), and the mixtures were created complex with PEI at different weight ratios (w/w) of poly(PEG-ApIm-PEG-Asp)/PEI$_{800}$ (w/w) in a various pH values solution for this measurement. Results were carried out in triplicate and the standard deviation is shown by the error bars.

Charge-Reversal Behavior of AAV2-poly(PEG-ApIm-PEG-Asp)/PEI$_{800}$ Complex at Physiologically Relevant pH Range The complex was measured by dynamic light scattering (DLS), and the success of the forming complex was verified by monitoring the changes in the surface charge using zeta potential measurements at various pH values. As expected, only poly(PEG-ApIm-PEG-Asp) existed in water at neutral pH displayed a negatively predicted value. The zeta potential for 10/1 to 1/1 varied between negative and positive values (−25.9±2.5 to 5.37±2.1 mV at pH 7.4) depending on the charge on the weight ratio of poly(PEG-ApIm-PEG-Asp)/PEI$_{800}$ (FIG. 5). Specifically, the extent of protonated amine groups of AAV2-poly(PEG-ApIm-PEG-Asp)/PEI$_{800}$ increases with decreasing the pH from 7.4 to 4.0, which, in turn, increases the positively-charged density on the complex due to the protonation of ApIm composite in poly(PEG-ApIm-PEG-Asp) and the second/tertiary amines of PEI$_{800}$.

More interestingly, the negatively charged AAV2-poly(PEG-ApIm-PEG-Asp)/PEI$_{800}$ complex (w/w, 5/1) over the positively charged complex was essential to change the pH value from 7.4 to 6.5, indicating that the in situ charge-reversal complex were performed in an in vivo relevant pH range of tumor. In addition, the complex delivered in specific site with a decrease in pH value for enhancement of complex closely interacted with negative charge of cellular membrane to deliver the AAV2.

Figure 6:
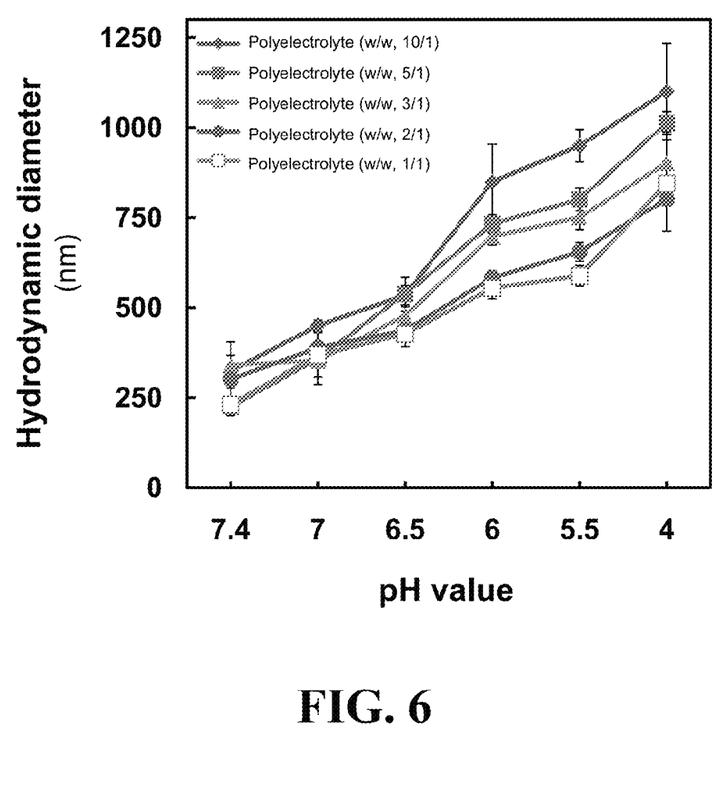
FIG. 6 is a plot of hydrodynamic diameter of AAV2-poly(PEG-ApIm-PEG-Asp)/PEI800 complex vs. pH variation according to one embodiment of the present disclosure. For preparation of the complex at different weight ratios (w/w), the AAV2 was first mixed with poly(PEG-ApIm-PEG-Asp), and the mixtures were created complex with PEI$_{800}$ at the weight ratio (w/w) of poly(PEG-ApIm-PEG-Asp)/PEI$_{800}$ in a various pH values solution for this measurement. Results were carried out in triplicate and the standard deviation is shown by the error bars.
Figure 7A:
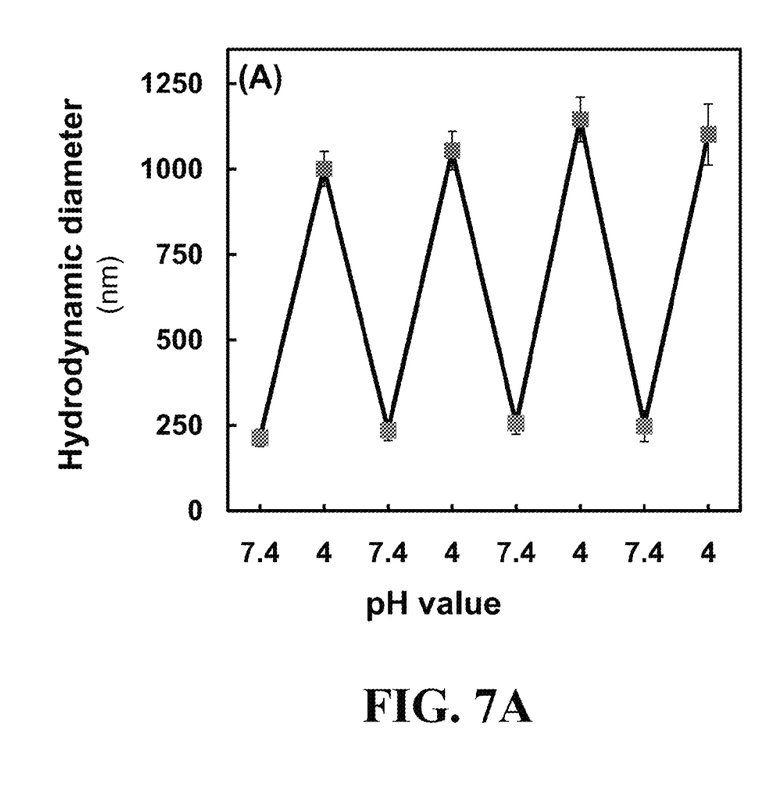
FIG. 7A shows the breathing behavior of AAV2-poly(PEG-ApIm-PEG-Asp)/PEI$_{800}$ complex via pH-dependent change according to one embodiment of the present disclosure. Reversible size of AAV2-poly(PEG-ApIm-PEG-Asp)/PEI$_{800}$ complex (w/w, 5/1) was changed between pH 7.4 and pH 4.0 for four cycles.
Figure 7B:
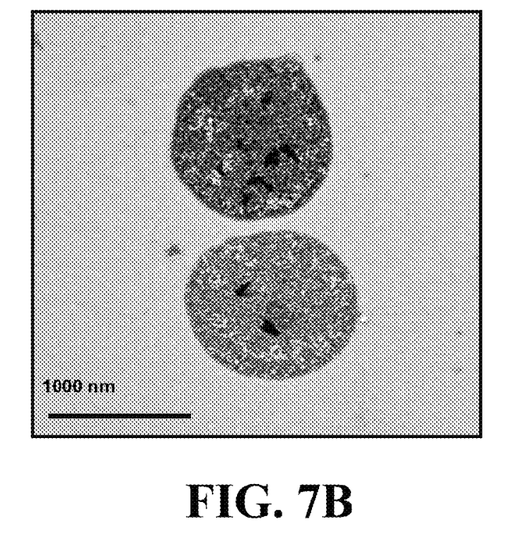
FIG. 7B shows TEM images of complex at pH 4.0 according to one embodiment of the present disclosure.
Figure 7C:
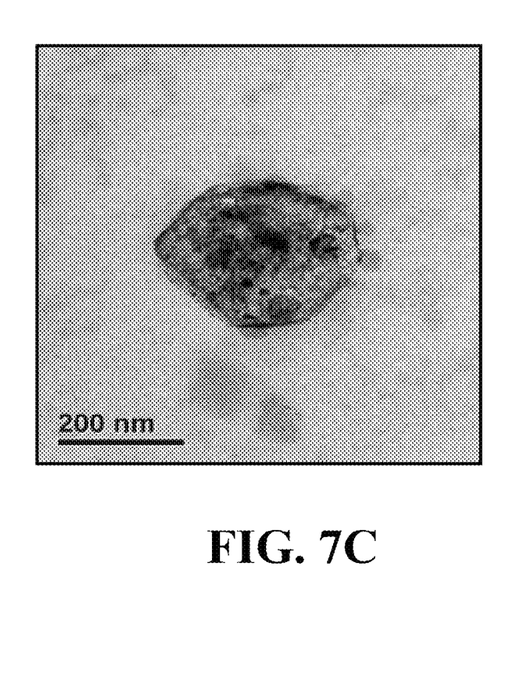
FIG. 7C shows TEM images of complex at pH 7.4 according to one embodiment of the present disclosure.

Size Oscillation of AAV2-poly(PEG-ApIm-PEG-Asp)/PEI$_{800}$ Complex at Physiologically Relevant pH Range The diameter of AAV2-poly(PEG-ApIm-PEG-Asp)/PEI$_{800}$ complex was monitored over a wide range of pH from 7.4 to 4.0. It can be observed that the size of AAV2-poly(PEG-ApIm-PEG-Asp)/PEI$_{800}$ complex (w/w, 5/1) increased steadily from 225±25 nm to 1,013±31 nm as the pH was decreased from 7.4 to 4.0 (FIG. 6). The pH-dependent size oscillation in the case of AAV2-poly(PEG-ApIm-PEG-Asp)/PEI$_{800}$ complex highlights the importance of poly(PEG-ApIm-PEG-Asp) and PEI$_{800}$ in this complex. The size oscillation of complex was repeatable for four cycles of pH changes between 7.4 and 4.0, and this is important that it occurs in a physiologically relevant pH range (FIG. 7A). This behavior can be considered breathing of pH-sensitive, and it is significant to note that the complex recovered and reformed the spherical complex in a pH 7.4 after they left the acidic pH environment. The AAV2-poly(PEG-ApIm-PEG-Asp)/PEI$_{800}$ complex was prepared as described above, and their TEM images are presented in FIGS. 7B and 7C. These TEM photographs clearly reveal that when the pH value was dropped from 7.4 to 4.0, the particle size of complex was increased.

pH-Dependence Transformation of AAV2-poly(PEG-ApIm-PEG-Asp)/PEI$_{800}$ Complex

Figure 8A:
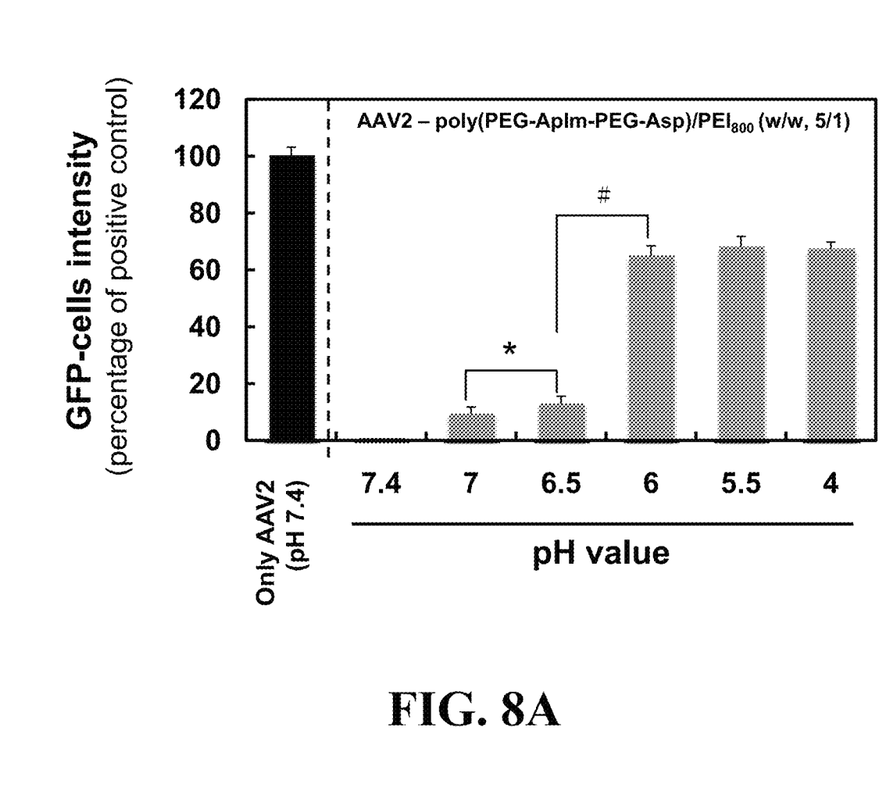
FIG. 8A shows GFP-transfected cells (%) of AAV2-poly(PEG-ApIm-PEG-Asp)/PEI$_{800}$ complex-mediated transformation at different pH values according to one embodiment of the present disclosure. For evaluation of AAV2 transformation, this assay used the AAV2-GFP encoding GFP (green fluorescent protein) reporter. Results were carried out in triplicate and the standard deviation is shown by the error bars.
Figure 8B:
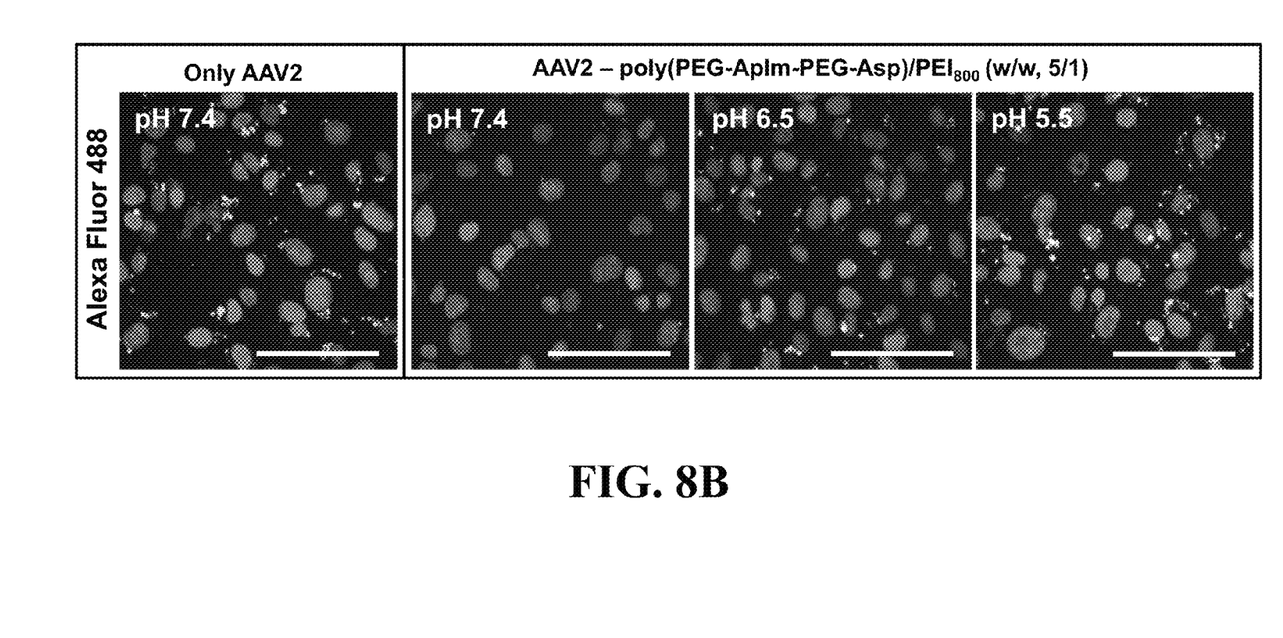
FIG. 8B shows a fluorescence micrograph of cellular uptake of Alexa Fluor 488 labled-AAV2 via delivery of AAV2-poly(PEG-ApIm-PEG-Asp)/PEI$_{800}$ complex (w/w, 5/1) through pH-dependence according to one embodiment of the present disclosure. The bars are 100 µm in length.
Figure 9:
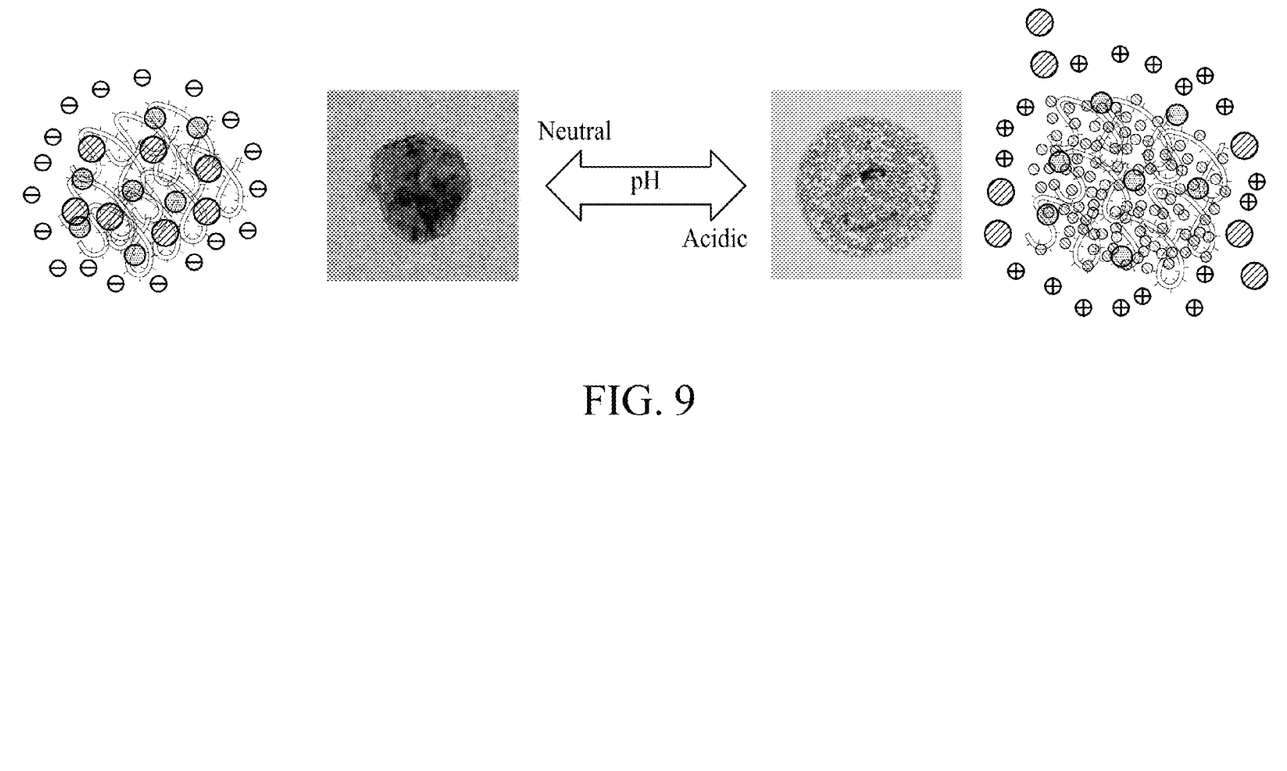
FIG. 9 shows swelling and deswelling of amines group inside the AAV2-poly(PEG-ApIm-PEG-Asp)/PEI$_{800}$ complex according to one embodiment of the present disclosure, which results in size changes of AAV2-poly(PEG-ApIm-PEG-Asp)/PEI$_{800}$ complex with respect to pH (water molecules surrounding protonated amine groups).

The pH-dependence release of AAV2-poly(PEG-ApIm-PEG-Asp)/PEI$_{800}$ polyelectrolytes at various pH values was evaluated by the AAV2-mediated transduction efficiency using flow cytometry analysis. In the poly(PEG-ApIm-PEG-Asp) copolymer, the tertiary amines of backbone or the unprotonation amine group of imidazole side-chain of ApIm were used to allow complex of AAV2 via electrostatic or hydrogen bond interactions. AAV2-poly(PEG-ApIm-PEG-Asp) complexes then form polyelectrolytes with cationic PEI$_{800}$ in neutral environment. However, when the ApIm (imidazole, pKa=6.0-6.5) and Asp (side chain of carboxylic acid, pKa=4.0; α-carboxylic acid, pKa$_2$=2.1) were used to study the release properties of AAV2-poly(PEG-ApIm-PEG-Asp)/PEI$_{800}$ polyelectrolytes, it shows the behaviors of GFP-transfect cells at different pH values (FIG. 8A). Using GFP as the reporter, about 13±2.6% GFP-transfected cells of the AAV2 was released even at pH 6.5, which was more or less equal to the amount released at pH 7.0 (P=0.35). Reducing the pH of the medium to 6.0 markedly increase the release of the AAV2 to lead the 65±3.5% GFP-transfected cells (P<0.005), a distinct deviation from the imidazole and PEI behavior. Specifically, the transduction efficiency increased with pH decreases from 7.4 to 5.5. A similar result of cellular uptake of AAV2 via AAV2-poly(PEG-ApIm-PEG-Asp)/PEI$_{800}$ polyelectrolytes delivery through pH-dependence conditions is illustrated in FIG. 8B, where the increase in Alexa Fluor 488 labled-AAV2 was confirmed by fluorescence microscopy. As a result, it was possible to successfully prevent the attachment of polyelectrolytes on cellular membrane via nanoparticle-mediated endocytsis or the release of AAV2 from polyelectrolytes when incubated at pH 7.4.

The pH-dependence release of AAV2 in the AAV2-poly(PEG-ApIm-PEG-Asp)/PEI$_{800}$ complex may be swollen with a pH decrease by the water uptake due to the protonated amine groups in their complex (FIG. 8). Furthermore, the size oscillation resulting from the degree of protonation of amine groups present in the polymeric system is effectively used to demonstrate a pH-dependent release of oppositely charged AAV2.

In conclusion, we have demonstrated for the first time pH-responsive complex to release the virus in a specific location. The complex was shown to reversibly expand and shrink in size by 4.5 times over a wide range of pH (7.4 to 4.0) due to the protonation of amino groups in the poly(PEG-ApIm-PEG-Asp) copolymer. The negatively charged complex over the positively charged complex was also critical in changing the pH value. The two unique behaviors of complex were used to demonstrate pH-dependent release of virus in the physiologically relevant pH range. It was also shown that the com- posite complex could be successfully used to delivery AAV2 quite effectively. The future development of this material could involve changing the hydrophobicity of the copolymer. The copolymer can load both hydrophobic and hydrophilic drugs. Furthermore, the complex can have special advantages over the existing carriers, as they can be loaded with two different kinds of guest molecules, reactants, or drugs for dual delivery applications.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A copolymer having the following chemical formula:

wherein R1 represents aliphatic compounds or aromatic compounds, R2 includes at least one negatively charged group, n is between 20 and 30, and m is between 2 and 10.

2. A composition comprising a plurality of copolymers of claim 1, wherein the plurality of copolymers has a weight-average molecular weight from 19,000 to 21,600 and a polydispersity index from 1.5 to 1.9.

3. The copolymer of claim 1, wherein the copolymer is negatively charged above pH 7.4.

4. The copolymer of claim 1, wherein the copolymer is positively charged below pH 6.5.

5. The copolymer of claim 1, wherein the negatively charged group is a carboxylate group.

6. A complex, comprising:
a plurality of positively charged polymers; and
a copolymer having the following chemical formula:

wherein R1 represents aliphatic compounds or aromatic compounds, R2 includes at least one negatively charged group, n is between 20 and 30, and m is between 2 and 10.

7. The complex of claim 6, comprising a plurality of the copolymer, wherein the plurality of the copolymer has a weight-average molecular weight from 19,000 to 21,600 and a polydispersity index from 1.5 to 1.9.

8. The complex of claim 6, wherein the copolymer is negatively charged above pH 7.4.

9. The complex of claim 6, wherein the copolymer is positively charged below pH 6.5.

10. The complex of claim 6, wherein the negatively charged group is a carboxylate group.

11. The complex of claim 6, wherein the size of the complex increases as the pH decreases from 7.4 to 4.0.

12. The complex of claim 6, wherein the positively charged polymers include polyethyleneimine.

13. A method for releasing viruses, comprising the steps of:
preparing a complex comprising a plurality of viruses, a plurality of polyethyleneimine particles, and a copolymer having the following chemical formula:

wherein R1 represents aliphatic compounds or aromatic compounds, R2 includes at least one negatively charged group, n is between 20 and 30, and m is between 2 and 10;

transferring the complex to an acidic region, thereby transforming the complex into a positively charged complex to release a portion of the viruses in the acidic region; and transferring the complex to a non-acidic region, thereby transforming the positively charged complex into a negatively charged complex.

14. The method for releasing viruses of claim 13, wherein the complex comprises a plurality of the copolymer, and wherein the plurality of the copolymer has a weight-average molecular weight from 19,000 to 21,600 and a polydispersity index from 1.5 to 1.9.

15. The method for releasing viruses of claim 13, wherein the copolymer is negatively charged above pH 7.4.

16. The method for releasing viruses of claim 13, wherein the copolymer is positively charged below pH 6.5.

17. The method for releasing viruses of claim 13, wherein the negatively charged group is a carboxylate group.

18. The method for releasing viruses of claim 13, wherein the size of the complex increases as the pH decreases from 7.4 to 4.0.

* * * * *